United States Patent [19]

Gericke et al.

[11] Patent Number: 4,937,257

[45] Date of Patent: Jun. 26, 1990

[54] FLAVANONE DERIVATIVES

[75] Inventors: Rolf Gericke, Seeheim; Helmut Wahlig, Darmstadt; Elvira Dingeldein, Dreieich, all of Fed. Rep. of Germany

[73] Assignee: Merck Patent Gesellschaft mit beschrankter Haftung, Darmstadt, Fed. Rep. of Germany

[21] Appl. No.: 770,327

[22] Filed: Aug. 28, 1985

[30] Foreign Application Priority Data

Aug. 28, 1984 [DE] Fed. Rep. of Germany ........ 3431534

[51] Int. Cl.$^5$ ..................... A61K 31/35; C07D 311/28
[52] U.S. Cl. ..................... 514/456; 514/100; 549/403; 549/220; 536/8; 536/13.2; 536/13.3; 536/13.6; 536/13.8; 536/16.6
[58] Field of Search ............... 549/403, 220; 514/456, 514/100; 536/8, 13.2, 13.3, 13.6, 13.8, 16.6

[56] References Cited

U.S. PATENT DOCUMENTS 3,678,044 7/1972 Adams ............................... 549/403
4,241,069 12/1980 Buckler et al. ...................... 549/403

OTHER PUBLICATIONS

Batterham et al., C.A., 61, 2620f (1964)–Abstract of Australian J. Chem., 17, 428 (1964).
Siekel et al., C.A. 57 12418(f), vol. 61 (1962).
Shah et al., C.A. 61 3008(f), vol. 61 (1964).
Martin Negwer, Organisch–Chemische Arzneimittel und Ihre Synonyma, pp. 699 and 940, 1978.

Primary Examiner—Nicky Chan
Attorney, Agent, or Firm—Millen, White & Zelano

[57] ABSTRACT

New flavanone derivatives of the formula I

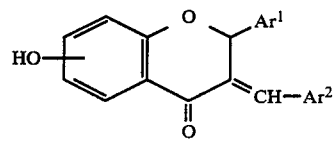

wherein Ar$^1$ and Ar$^2$ are each phenyl which is unsubstituted or monosubstituted to trisubstituted by OH, alkyl, alkoxy, acylamino, halogen, COOalkyl and/or NO$_2$ and/or substituted by a methylenedioxy group, and the alkyl, alkoxy and acyl groups each have 1–7 C atoms, but wherein the HO group is only in the 6-position if at least one of the radicals Ar$^1$ and Ar$^2$ is substituted phenyl, and the phosphoric acid esters thereof and the salts of these compounds display antiallergic effects. Salts of the I-phosphoric acid esters with aminoglycoside antibiotics are outstandingly stable and possess advantageous kinetics of liberation.

24 Claims, No Drawings

FLAVANONE DERIVATIVES

The invention relates to new flavanone derivatives.

SUMMARY OF THE INVENTION

It is an object of this invention to provide new compounds having valuable properties, particularly compounds which can be used for the preparation of medicaments.

Upon further study of the specification and appended claims, further objects and advantages of this invention will become apparent to those skilled in the art.

These objects have been achieved by providing new flavanone derivatives of the formula

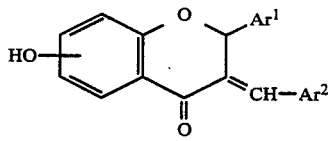

wherein $Ar^1$ and $Ar^2$ are independently each phenyl which is unsubstituted or monosubstituted to trisubstituted by OH, alkyl, alkoxy, acylamino, halogen, COOalkyl and/or $NO_2$ and/or substituted by methylenedioxy, and the alkyl, alkoxy and acyl groups each have 1–7 C atoms, but wherein the HO group on the benzo ring is in the 6-position only if at least one of the radicals $Ar^1$ and $Ar^2$ is substituted phenyl, and their phosphoric acid esters ("I-phosphates") and the salts of these compounds.

DETAILED DISCUSSION

It has been found that the compounds of the formula I and their phosphoric acid esters and the salts of these compounds possess valuable pharmacological properties. Thus they display, for example, anti-allergic effects which can be demonstrated, for example, by intravenous adminstration to rats. Conventional methods for demonstrating this effect are described, for example, in the literature which is quoted in European Patent Application 0,056,475.

In particular, however, certain sparingly soluble salts of the I-phosphates are important, namely those derived from aminoglycoside antibiotics. These salts also display antibiotic effects, but are distinguished by slower liberation of the active compound.

Flavanoid phosphates of aminoglycoside antibiotics having similar properties are mentioned in German Offenlegungsschrift 3,206,725 (U.S. Ser. No. 613,131 of May 23, 1984, a continuation-in-part of Ser. No. 377,779 of May 13, 1982). However, at no point are references found to the particularly advantageous salts with the present I-phosphates, which are distinguished by outstanding stability and advantageous kinetics of liberation. In addition, they contain an acid component which can be defined more exactly than hesperidin phosphate, which is described in the reference and indicated as particularly preferred.

The compounds of the formula I, their phosphates and the salts of these compounds can, therefore, be used as medicinal active compounds in human and veterinary medicine. The flavanones I themselves and the I-phosphates are also used as intermediate products, in particular for the preparation of the said salts.

In the formula I, the radicals $Ar^1$ and $Ar^2$ are preferably identical; they can, however, also be different from one another. Preferably they are phenyl groups which are monosubstituted, preferably in the p-position, but also in the o-position or m-position; they can, however, also be unsubstituted phenyl groups and phenyl groups which are disubstituted, preferably in the 3,4-position, but also in the 2,3- 2,4-, 2,5-, 2,6- or 3,5-position, or trisubstituted, preferably in the 3,4,5-position, but also in the 2,3,4-, 2,3,5-, 2,3,6-, 2,4,5- or 2,4,6-position.

The alkyl, alkoxy and acyl (e.g., alkanoyl) groups in the radicals $Ar^1$ and $Ar^2$ each contain 1–7, preferably each 1–4, and especially 1 or 2, C atoms.

The particularly preferred alkyl groups in the radicals $Ar^1$ and $Ar^2$ are methyl and ethyl and also propyl, isopropyl, butyl, isobutyl, sec.-butyl, tert.-butyl and also pentyl, isopentyl (=3-methylbutyl), hexyl, isohexyl (=4-methylpentyl) and heptyl; particularly preferred alkoxy groups are methoxy and ethoxy, and also propoxy, isopropoxy, butoxy, isobutoxy, sec.-butoxy, tert.-butoxy and also pentoxy, isopentoxy (=3-methylbutoxy), hexoxy, isohexoxy (=4-methylpentoxy) and heptoxy, and particularly preferred acylamino groups are formamido and acetamido, and also propionamido, butyramido, isobutyramido and also valeramido, isovaleramido, trimethylacetamido, hexanamido, tert.-butylacetamido and heptanamido. Halogen is preferably Cl, but also F, Br or I; COOalkyl is preferably methoxycarbonyl or ethoxycarbonyl and also propoxycarbonyl, isopropoxycarbonyl, butoxycarbonyl, isobutoxycarbonyl and also sec.-butoxycarbonyl, tert.-butoxycarbonyl, pentoxycarbonyl, hexoxycarbonyl or heptoxycarbonyl.

Specifically, $Ar^1$ and/or $Ar^2$ are preferably p-methoxyphenyl, and also phenyl, o-, m- or p-hydroxyphenyl, o-, m- or p-tolyl, o-, m- or p-ethylphenyl, o-, m- or p-propylphenyl, o-, m- or p-isopropylphenyl, o-methoxyphenyl or m-methoxyphenyl, o-, m- or p-ethoxyphenyl, o-, m- or p-formamidophenyl, o-, m- or p-acetamidophenyl, o-, m- or p-fluorophenyl, o-, m- or p-chlorophenyl, o-, m- or p-bromophenyl, o-, m- or p-iodophenyl, o-, m- or p-methoxycarbonylphenyl, o-, m- or p-ethoxycarbonylphenyl, o-, m- or p-nitrophenyl, 2,3-methylenedioxyphenyl or 3,4-methylenedioxyphenyl, 2,3-, 2,4- 2,5-, 2,6-, 3,4- or 3,5-dimethoxyphenyl, 2,3- 2,4-, 2,5-, 2,6-, 3,4- or 3,5-dichlorophenyl, 3,4,5-trimethoxyphenyl, 3-hydroxy-4-methoxyphenyl or 3-methoxy-4-hydroxyphenyl.

The HO group in formula I is preferably in the 6-position, but it can also be in the 5-, 7- or 8-position.

Accordingly, the invention relates in particular to compounds of the formula I, and to their phosphates and the salts of these compounds, in which at least one of the said radicals has one of the preferred meanings mentioned above and/or is in one of the positions indicated as preferred. Some preferred groups of compounds can be expressed by the following partial formulae Ia to Il, which correspond to the formula I and wherein the radicals not designated in detail have the meanings indicated in the formula I, but wherein:

in Ia $Ar^1$ is phenyl or phenyl which is monosubstituted by OH, alkyl, alkoxy or acylamino each of which has 1–4 C atoms, F, Cl, Br, I, COOalkyl wherein the alkyl group contains 1–4 C atoms, $NO_2$ or methylenedioxy, or disubstituted by alkoxy having 1–4 C atoms or by Cl, or trisubstituted, by alkoxy;

in Ib $Ar^1$ is phenyl, isopropylphenyl, methoxyphenyl, acetamidophenyl, chlorophenyl, dichlorophenyl or trimethoxyphenyl;

in Ic $Ar^1$ is phenyl or methoxyphenyl;

in Id $Ar^1$ is p-methoxyphenyl;

in Ie $Ar^2$ is phenyl or phenyl which is monosubstituted by OH, alkyl, alkoxy or acylamino each of which has 1–4 C atoms, F, Cl, Br, I, COOalkyl wherein the alkyl group contains 1–4 C atoms, $NO_2$ or methylenedioxy, or disubstituted by alkoxy having 1–4 C atoms or Cl, or trisubstituted by alkoxy;

in If $Ar^2$ is phenyl, isopropylphenyl, methoxyphenyl, acetamidophenyl, chlorophenyl, dichlorophenyl or trimethoxyphenyl;

in Ig $Ar^2$ is phenyl or methoxyphenyl;

in Ih $Ar^2$ is p-methoxyphenyl;

in Ii $Ar^1$ and $Ar^2$ are each phenyl or phenyl which is monosubstituted by OH, alkyl, alkoxy or acylamino each of which has 1–4 C atoms, F, Cl, Br, I, COOalkyl wherein the alkyl group contains 1–4 C atoms, $NO_2$ or methylenedioxy, or disubstituted by alkoxy having 1–4 C atoms or Cl, or trisubstituted by alkoxy;

in Ij $Ar^1$ and $Ar^2$ are each phenyl, isopropylphenyl, methoxyphenyl, acetamidophenyl, chlorophenyl, dichlorophenyl or trimethoxyphenyl;

in Ik $Ar^1$ and $Ar^2$ are each phenyl or methoxyphenyl; and in Il $Ar^1$ and $Ar^2$ are each p-methoxyphenyl.

Compounds which are also particularly preferred are those of the formulae Iaa and Ika, which correspond to the formulae Ia to Ik, but wherein $Ar^1$ is $Ar^2$, and also compounds of the formula Iab to Ilb and Iaab to Ikab, which correspond to the formulae Ia to Il and to Iaa to Ika, but wherein the HO group is in the 6-position of the flavanone system.

The phosphates of compounds of the formula Ia to Il, Iaa to Ika, Iab to Ilb and Iaab to Ikab and the salts of these compounds, in particular the salts with aminoglycoside antibiotics, are also particularly preferred.

The compounds of the formula I, their phosphates and the salts of these compounds can exist in the cis-configuration and in the trans-configuration. The trans-configuration is preferred. Unless anything to the contrary is indicated below, the substances indicated are always the trans-isomers. However, the cis-isomers are also included in the formulae of the compounds according to the invention; they can be obtained from the trans-isomers by irradiation (for method cf. J. Org. Chem. 35, 2286 (1970)). The formulae of the compounds according to the invention also embrace mixtures of isomers.

The invention also relates to a process for the preparation of flavanone derivatives of the formula I, characterized in that a flavanone of the formula II

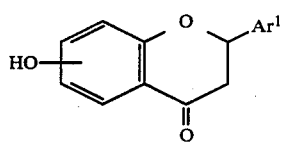   II wherein $Ar^1$ has the meaning indicated in formula I is reacted with an aldehyde of the formula III

   III wherein $Ar^2$ has the meaning indicated in formula I, or a chalcone of the formula IV

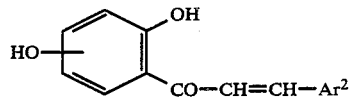   IV wherein $Ar^2$ has the meaning indicated in formula I is reacted with an aldehyde of the formula V

   V wherein $Ar^1$ has the meaning indicated in formula I, and/or a hydroxyflavanone of the formula I is converted into the corresponding phosphoric acid ester by treatment with a phosphorylating agent, and/or a compound of the formula I is converted into one of its salts by treatment with a base.

The compounds of the formula I are, moreover, prepared by methods which are in themselves known, such as are described in the literature (for example in the standard works such as Houben-Weyl, Methoden der Organischen Chemie ("Methods of Organic Chemistry"), Georg-Thieme Verlag, Stuttgart; or Organic Reactions, John Wiley & Sons, Inc., New York), specifically under reaction conditions which are known and suitable for the said reactions. In this respect it is also possible to make use of variants which are in themselves known and are not mentioned here in detail.

If desired, the starting materials can also be formed in situ, in such a way that they are not isolated from the reaction mixture, but are immediately reacted further to give the compounds of the formula I.

Thus, the compounds of the formula I are preferably prepared by reacting dihydroxyacetophenones of the formula VI

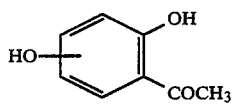   VI with aldehydes of the formula III or V, in the course of which the flavanones II and/or the chalcones IV are formed as intermediate products, but are not isolated. In particular, compounds of the formulae I wherein $Ar^1$ is $Ar^2$, and Iaa to Ika can be obtained advantageously in this way.

The starting materials of the formulae II to VI are for the most part known (cf., for example, U.S. Patent Specification 3,450,717). Insofar as they are not known, they can be prepared by methods which are in themselves known. Thus the starting materials of the formulae II or IV can be obtained from dihydroxyacetophenones of the formula VI by means of aldehydes of the formulae V or III.

Specifically, the reactions of II with III, IV with V or VI with III or V are carried out in the presence or absence of an inert solvent, for example an alcohol such as methanol, ethanol or isopropanol, an ether such as tetrahydrofuran or dioxane, an ester such as ethyl acetate, or in mixtures of these solvents with one another and/or with water, at temperatures between about 0° and about 150°, preferably between 15° and 100°.

It is preferable, even if not absolutely necessary, to carry out the reaction in the presence of an acid or basic catalyst, for example a mineral acid such as hydrochloric acid, hydrobromic acid, sulphuric acid or phosphoric acid, an organic sulphonic acid such as methanesulphonic or p-toluenesulphonic acid, an alkali metal hydroxide such as NaOH or KOH, an amide such as $NaNH_2$, a hydride such as NaH or an amine such as piperidine, triethylamine or pyridine. An excess of the catalyst can also be used as a solvent in individual cases.

The I-phosphates can preferably be obtained by treating the hydroxyflavanones of the formula I with phosphorylating agents. If one or more OH groups are present in the radicals $Ar^1$ and/or $Ar^2$ of the starting material I, these can also be phosphorylated, so that the corresponding I-diphosphates, I-triphosphates and the like are obtained.

Besides free phosphoric acid, phosphorylating agents are, above all, pyrophosphoric acid, polyphosphoric acid, phosphorus pentoxide, phosphorus oxychloride, monochlorophosphoric acid (a mixture of orthophosphoric acid and phosphorus oxychloride), phosphoric acid monobenzyl ester, phosphoric acid dibenzyl esterchloride, phosphoric acid mono-(2-cyanoethyl ester) and phosphoric acid dimorpholide-chloride.

The phosphorylation of the hydroxyflavanone of the formula I is effected in the absence or presence of an additional solvent. Suitable solvents are preferably organic bases, such as pyridine, triethylamine, quinoline, dimethylaniline or diethylaniline, if an acid, for example hydrogen chloride, is split off in the reaction. In other cases or additionally it is possible to use inert organic solvents, such as, for example, diethyl ether, diisopropyl ether, tetrahydrofuran, dioxane, chloroform, methylene chloride, trichloroethylene, dimethylformamide, dimethyl sulphoxide, benzene, toluene, xylene, tetralin or acetonitrile. It is also possible to use mixtures of the above bases and/or solvents. It is also possible to carry out the reaction in an excess of the phosphorylating agent. The reaction temperatures are between $-80°$ and $+200°$, preferably between $-10°$ and $+100°$.

Very generally, it is possible to use the processes described in Houben-Weyl, l.c., volume XII/2, pages 143-210 (1964), for the preparation of the I-phosphates and their salts.

Intermediate products containing protective groups can be formed during the preparation of the compounds of the formula I and their phosphoric acid esters. These groups can be removed by hydrolysis or hydrogenolysis. In particular, protected hydroxyl groups can be set free by alkaline hydrolysis or by careful acid hydrolysis. Protected hydroxyl groups of this type can originate from the flavanoid component, but preferably from the phosphoric acid component in the esterification reaction. For example, if esterification has been carried out with phosphoric acid mono-(2-cyanoethyl ester), phosphoric acid diphenyl ester-chloride or phosphoric acid dimorpholide-chloride, the resulting phosphoric acid diesters or triesters or monoester-diamides can be split by means of, for example, alkali metal hydroxide or ammonium hydroxide solutions or basic or acid ion exchangers to give the desired flavanoid phosphoric acid esters.

Protective groups, preferably benzyl groups in phosphoric acid esters, can be split off by hydrogenolysis, for example by catalytic hydrogenation, preferably under mild conditions, for example by means of a palladium catalyst, such as palladium on charcoal, calcium carbonate or strontium carbonate, and at room temperature and normal pressure, the hydrogenation being preferably discontinued after the calculated amount of hydrogen has been absorbed.

The hydroxyflavanones of the formula I and their phosphoric acid esters can be converted into the corresponding salts by treatment with a base. Suitable salts are the phenolates of hydroxyflavanone I, but above all the salts of the I-phosphates. Physiologically acceptable salts are preferred. As a rule, the salts are prepared at room temperature, and the solvents used are especially water, alcohols, such as methanol or ethanol, mixtures of water with alcohols or the bases employed for the formation of the salt. Bases which are preferentially suitable are the hydroxides, carbonates or alcoholates of the alkali and alkaline earth metals and also the corresponding ammonium compounds, preferably sodium hydroxide, carbonate, bicarbonate, methylate, ethylate, isopropylate or tert.-butylate, potassium hydroxide, carbonate, bicarbonate, methylate, ethylate, isopropylate or tert.-butylate, calcium hydroxide, carbonate, bicarbonate, methylate, ethylate, isopropylate or tert.-butylate, magnesium hydroxide, carbonate, bicarbonate, methylate, ethylate, isopropylate or tert.-butylate, and also ammonium hydroxide, carbonate or bicarbonate as well as substituted ammonium hydroxides, carbonates or bicarbonates.

Salts of the I-phosphates with aminoglycoside antibiotics are, however, of particular importance.

Suitable aminoglycoside antibiotics are especially those containing a deoxystreptamine unit. Specifically, amicacin, dibecacin, gentamycin, neomycins, paromomycin, sagamycin, sisomicin, streptomycin and tobramycin are particularly preferred, and the following, for example, are also preferred: allomycin, amicetin, apramycin, becanamycin, betamicin, butirosin, destomycin, everninomycins, ezomycins, flambamycin, fortimycin A and B, framycetin, hikizimycin, homomycin, hybrimycin, hygromycin, kanamycins, kasugamycin, lividomycin, minosaminomycin, myomycins, netilmicin, parvulomycin, puromycin A, ribostamycin, rimocidin, ristomycin, ristosamin, seldomycins, sorbistin, spectinomycin, streptothricin, tunicamycin and verdamycin and epimers and derivatives thereof, provided that they are basic. See, e.g., *Aminoglycitol Antibiotics*, Rinehart et al, Ed., ACS, Washington, D.C. (1980).

Since some of these antibiotics, for example gentamycin, are known not to be unitary substances, but represent mixtures (gentamycin, for example, is a mixture of the compounds gentamycin C 1, gentamycin C 2 and gentamycin C 1a), the salts of the I-phosphates are also not unitary substances, but mixtures, in individual cases. Since many of the antibiotics mentioned, for example all the gentamycins, contain several basic nitrogen atoms, and since, on the other hand, the I-phosphates are polybasic acids, it is also possible for acid, neutral and/or basic salts to be formed. All these possible salts and mixtures thereof with one another are embraced in the definition "salts of the phosphoric acid esters of flavanones of the formula I with aminoglycoside antibiotics".

The neutral salts and mixtures containing the latter are preferred; in the case of the gentamycin salts for example, the salts (mixtures) composed of 1 mole of gentamycin and 3 to 5, particularly about 4, moles of I-phosphate are particularly preferred, especially the salt composed of 1 mole of gentamycin and about 4 moles of 3-p-methoxybenzylidene-6-hydroxy-4'-methoxyflavanone-6-phosphate; this salt is designated "G" below. The acid protons of the salt which have not been neutralized by the amino groups of the antibiotic can be present in the free (acid) form or can be neutralized by means of sodium ions or other physiologically acceptable ions.

The salts of the I-phosphates with the aminoglycoside antibiotics are prepared in a manner which is in itself known, for instance by combining an aqueous solution of a water-soluble salt of the antibiotic (for example gentamycin sulphate) with an aqueous solution of the I-phosphate or one of its water-soluble salts (for example the disodium salt), preferably with stirring at room temperature at pH values between 4 and 8. It is also possible to add an organic solvent, for example an alcohol, such as ethanol, in order to improve the solubility. The resulting antibiotic salts are sparingly soluble in water and can be obtained by filtration, washing with water and drying.

The compounds of the formula I and their phosphates can possess one or more centers of asymmetry. When they are prepared, therefore, they can be obtained as racemates or, it optically active starting materials are used, also in an optically active form. If the compounds have two or more centers of asymmetry, they are generally obtained in the synthesis as mixtures of racemates, from which the individual racemates can be isolated in a pure form, for example by recrystallization from inert solvents. Resulting racemates can, if desired, be resolved into their optical antipodes mechanically or chemically by methods which are in themselves known. Preferably, diastereomers are formed from the racemate by reacting the latter with an optically active resolving agent. Examples of suitable resolving agents, especially for the I-phosphates, are optically active bases, for example quinine, quinidine, cinchonine, cinchonidine, brucine, dihydroabietylamine, strychnine, morphine or the D- and L-forms of 1-phenylethylamine, fenchylamine or menthylamine or of basic amino acids, for example arginine or lysine, or of esters thereof. The various forms of the diastereomers can be separated in a manner which is in itself known, for example by fractional crystallization, and the optically active compounds of the formula I or phosphates thereof can be liberated from the diastereomers in a manner which is in itself known.

The invention also relates to the use of the compounds of the formula I, their phosphoric acid esters and the salts of these compounds, above all the salts mentioned with aminoglycoside antibiotics, for the preparation of pharmaceutical formulations, especially by a non-chemical route. This can be effected by bringing them into a suitable dosage form together with at least one solid, liquid or semi-liquid excipient or auxiliary and, if appropriate, in combination with one or more further active compound(s).

The invention also relates to pharmaceutical formulations containing at least one compound of the formula I and/or one of its phosphoric acid esters and/or a physiologically acceptable salt of one of these compounds.

These formulations can be used as medicaments in human or veterinary medicine. Suitable excipients are organic or inorganic substances which are suitable for enteral (for example oral) and parenteral administration or topical application and which do not react with the new compounds, for example water, vegetable oils, benzyl alcohols, polyethylene glycols, glycerol triacetate, gelatin, carbohydrates, such as lactose or starch, magnesium stearate, talc or petroleum jelly. Tablets, coated tablets, capsules, syrups, elixirs or drops are used especially for oral administration, suppositories are used for rectal administration, solutions, suspensions, emulsions or implants are used for parenteral administration, and ointments, creams or powders are used for topical application. Implants, for example those based on silicone rubber, tricalcium phosphate or collagen, which are suitable, for example, for the treatment of infected bone, are of particular importance, especially for the antibiotic salts mentioned. The antibiotic is set free in a protracted manner from these implants, so that effective levels of the antibiotic are present in the neighborhood of the implant for a long sustained period. Fibrin-antibiotic gels, such as are described, for example, in German Offenlegungsschrift 3,206,725, are also suitable for therapeutic administration. The new compounds can also by lyophilized, and the resulting lyophilizates can be used, for example, for the preparation of injection formulations. The formulations indicated can be sterilized and/or can contain auxiliaries such as lubricants, preservatives, stabilizers and/or wetting agents, emulsifiers, salts for influencing the osmotic pressure, buffer substances, colorants, flavorings and/or aroma substances. If desired, they can also contain one or more further active compounds; formulations containing antibiotic salts of the I-phosphates can, for example, additionally contain readily soluble salts of the same or other antibiotics in order to achieve a systemic action in addition to the depot effect produced by the salts of the I-phosphates.

The invention also relates to the use of the compounds of the formula I, their phosphoric acid esters and/or the physiologically acceptable salts of these compounds in combating diseases, in particular allergies and/or bacterial infections, and to their use in the therapeutic treatment of the human or animal body.

In this respect, the substances according to the invention are, as a rule, administered analogously to known, commercially available antiallergics or bronchospasmolytics/antiasthmatics, for example cromoglycic acid and salts thereof, or antibiotics, preferably in dosages between about 5 and 1,000 mg, especially between 10 and 500 mg, per dosage unit (in the case of the antibiotic salts, relative to the antibiotic active compound). The particular dose for each specific patient depends, however, on a very wide variety of factors, for example on the effectiveness of the particular compound employed, on the age, body weight, general state of health and sex, on the diet, on the time and mode of administration, and on the excretion rate, the combination of medicaments and the severity of the particular disease for which the therapy is applicable. Local administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

IR=maxima of the infrared spectrum in KBr.

EXAMPLE 1

HCl is passed for 4 hours, with stirring, into a solution of 15.2 g of 2,5-dihydroxyacetophenone and 27.2 g of anisaldehyde in 1,500 ml of ethanol. 3-p-Methoxybenzylidene-6-hydroxy-4'-methoxyflavanone is precipitated, m.p. 199°–201°. 6-Hydroxy-4'-methoxyflavanone and 2,5-dihydroxy-p-methoxybenzylideneacetophenone are formed as intermediates.

The following can be obtained analogously by means of the corresponding aldehydes:
3-o-Hydroxybenzylidene-6,2'-dihydroxyflavanone
3-m-Hydroxybenzylidene-6,3'-dihydroxyflavanone
3-p-Hydroxybenzylidene-6,4'-dihydroxyflavanone
3-p-Methylbenzylidene-6-hydroxy-4'-methylflavanone
3-p-Ethylbenzylidene-6-hydroxy-4'-ethylflavanone
3-p-Ethylbenzylidene-6-hydroxy-4'-ethylflavanone
3-p-Isopropylbenzylidene-6-hydroxy-4'-isopropylflavanone, m.p. 178°–180°
3-o-Methoxybenzylidene-6-hydroxy-2'-methoxyflavanone
3-m-Methoxybenzylidene-6-hydroxy-3'-methoxyflavanone
3-p-Methoxybenzylidene-5-hydroxy-4'-methoxyflavanone
3-p-Methoxybenzylidene-7-hydroxy-4'-methoxyflavanone
3-p-Methoxybenzylidene-8-hydroxy-4'-methoxyflavanone
3-(3,4-Dimethoxybenzylidene)-6-hydroxy-3',4'-dimethoxyflavanone
3-(3,4,5-Trimethoxybenzylidene)-6-hydroxy-3',4',5'-trimethoxyflavanone, m.p. 168°–170°
3-p-Acetamidobenzylidene-6-hydroxy-4'-acetamidoflavanone, m.p. 205°
3-p-Fluorobenzylidene-6-hydroxy-4'-fluoroflavanone
3-p-Chlorobenzylidene-6-hydroxy-4'-chloroflavanone
3-(3,4-Dichlorobenzylidene)-6-hydroxy-3',4'-dichloroflavanone, m.p. 228°–230°
3-p-Bromobenzylidene-6-hydroxy-4'-bromoflavanone
3-p-Iodobenzylidene-6-hydroxy-4'-iodoflavanone
3-p-Methoxycarbonylbenzylidene-6-hydroxy-4'-methoxycarbonylflavanone (methanol is used as the solvent)
3-p-(Ethoxycarbonylbenzylidene-6-hydroxy-4'-ethoxycarbonylflavanone
3-o-Nitrobenzylidene-6-hydroxy-2'-nitroflavanone
3-m-Nitrobenzylidene-6-hydroxy-3'-nitroflavanone
3-p-Nitrobenzylidene-6-hydroxy-4'-nitroflavanone
3-(3,4-Methylenedioxybenzylidene)-6-hydroxy-3',4'-methylenedioxyflavanone.

EXAMPLE 2

A hot solution of 27 g of 6-hydroxy-4'-methoxyflavanone and 13.6 g of anisaldehyde in 1,400 ml of ethanol is saturated with HCl and is left for 3 hours to cool; precipitation with water gives 3-p-methoxybenzylidene-6-hydroxy-4'-methoxyflavanone, m.p. 199°–201°.

The compounds indicated in Example 1 can be obtained analogously from the corresponding 6-hydroxyflavanones and the corresponding aldehydes.

The following can also be obtained analogously:
3-Benzylidene-5-hydroxyflavanone
3-Benzylidene-7-hydroxyflavanone
3-Benzylidene-8-hydroxyflavanone
3-p-Methoxybenzylidene-5-hydroxyflavanone
3-p-Methoxybenzylidene-6-hydroxyflavanone
3-p-Methoxybenzylidene-7-hydroxyflavanone
3-p-Methoxybenzylidene-8-hydroxyflavanone
3-Benzylidene-5-hydroxy-4'-methoxyflavanone
3-Benzylidene-6-hydroxy-4'-methoxyflavanone
3-Benzylidene-7-hydroxy-4'-methoxyflavanone
3-Benzylidene-8-hydroxy-4'-methoxyflavanone
3-o-Hydroxybenzylidene-6-hydroxy-4'-methoxyflavanone
3-m-Hydroxybenzylidene-6-hydroxy-4'-methoxyflavanone
3-p-Hydroxybenzylidene-6-hydroxy-4'-methoxyflavanone
3-(2,4-Dihydroxybenzylidene)-6-hydroxy-4'-methoxyflavanone
3-(3-Methoxy-4-hydroxybenzylidene)-6-hydroxy-4'-methoxyflavanone
3-o-Methylbenzylidene-6-hydroxy-4'-methoxyflavanone
3-m-Methylbenzylidene-6-hydroxy-4'-methoxyflavanone
3-p-Methylbenzylidene-6-hydroxy-4'-methoxyflavanone
3-p-Isopropylbenzylidene-6-hydroxy-4'-methoxyflavanone
3-p-Heptylbenzylidene-6-hydroxy-4'-methoxyflavanone
3-o-Methoxybenzylidene-6-hydroxy-4'-methoxyflavanone
3-m-Methoxybenzylidene-6-hydroxy-4'-methoxyflavanone
3-p-Ethoxybenzylidene-6-hydroxy-4'-methoxyflavanone
3-p-Heptoxybenzylidene-6-hydroxy-4'-methoxyflavanone
3-(3,4-Dimethoxybenzylidene)-6-hydroxy-4'-methoxyflavanone
3-(3,4,5-Trimethoxybenzylidene)-6-hydroxy-4'-methoxyflavanone
3-p-Formamidobenzylidene-6-hydroxy-4'-methoxyflavanone
3-o-Acetamidobenzylidene-6-hydroxy-4'-methoxyflavanone
3-m-Acetamidobenzylidene-6-hydroxy-4'-methoxyflavanone
3-p-Acetamidobenzylidene-6-hydroxy-4'-methoxyflavanone
3-p-Propionamidobenzylidene-6-hyroxy-4'-methoxyflavanone
3-p-Butyramidobenzylidene-6-hydroxy-4'-methoxyflavanone
3-p-Heptanamidobenzylidene-6-hydroxy-4'-methoxyflavanone
3-p-Benzamidobenzylidene-6-hydroxy-4'-methoxyflavanone
3-p-Fluorobenzylidene-6-hyroxy-4'-methoxyflavanone
3-p-Chlorobenzylidene-6-hydroxy-4'-methoxyflavanone
3-(3,4-Dichlorobenzylidene)-6-hydroxy-4'-methoxyflavanone
3-p-Bromobenzylidene-6-hydroxy-4'-methoxyflavanone
3-p-Iodobenzylidene-6-hydroxy-4'-methoxyflavanone
3-p-Methoxycarbonylbenzylidene-6-hydroxy-4'-methoxyflavanone
3-p-Ethoxycarbonylbenzylidene-6-hydroxy-4'-methoxyflavanone
3-o-Nitrobenzylidene-6-hydroxy-4'-methoxyflavanone
3-m-Nitrobenzylidene-6-hydroxy-4'-methoxyflavanone
3-p-Nitrobenzylidene-6-hydroxy-4'-methoxyflavanone
3-(3,4-Methylenedioxybenzylidene)-6-hydroxy-4'-methoxyflavanone.

EXAMPLE 3

A mixture of 2.7 g of 2,5-dihydroxy-p-methoxybenzylidene aceto-phenone, 1.36 g of anisaldehyde and 5 ml of piperidine is heated at 100° for 1 hour and is cooled, and water is added. 3-p-Methoxybenzylidene-6- hydroxy-4'-methoxyflava-none is precipitated; m.p. 199°–201°.

The following can be obtained analogously by means of the corresponding aldehydes:
3-p-Methoxybenzylidene-6-hydroxyflavanone
3-p-Methoxybenzylidene-6,2'-dihydroxyflavanone
3-p-Methoxybenzylidene-6,3'-dihydroxyflavanone
3-p-Methoxybenzylidene-6,4'-dihydroxyflavanone
3-p-Methoxybenzylidene-6,3',4'-trihydroxyflavanone
3-p-Methoxybenzylidene-6,4'-dihydroxy-3'-methoxyflavanone
3-p-Methoxybenzylidene-6-hydroxy-2'-methylflavanone
3-p-Methoxybenzylidene-6-hydroxy-3'-methylflavanone
3-p-Methoxybenzylidene-6-hydroxy-4'-methylflavanone
3-p-Methoxybenzylidene-6-hydroxy-4'-isopropylflavanone
3-p-Methoxybenzylidene-6-hydroxy-4'-heptylflavanone
3-p-Methoxybenzylidene-6-hydroxy-2'-methoxyflavanone
3-p-Methoxybenzylidene-6-hydroxy-3'-methoxyflavanone
3-p-Methoxybenzylidene-6-hydroxy-4'-ethoxyflavanone
3-p-Methoxybenzylidene-6-hydroxy-4'-heptoxyflavanone
3-p-Methoxybenzylidene-6-hydroxy-3',4'-dimethoxyflavanone
3-p-Methoxybenzylidene-6-hydroxy-3',4',5'-trimethoxyflavanone
3-p-Methoxybenzylidene-6-hydroxy-4'-formamidoflavanone
3-p-Methoxybenzylidene-6-hydroxy-2'-acetamidoflavanone
3-p-Methoxybenzylidene-6-hydroxy-3'-acetamidoflavanone
3-p-Methoxybenzylidene-6-hydroxy-4'-acetamidoflavanone
3-p-Methoxybenzylidene-6-hydroxy-4'-propionamidoflavanone
3-p-Methoxybenzylidene-6-hydroxy-4'-butyramidoflavanone
3-p-Methoxybenzylidene-6-hydroxy-4'-heptanamidoflavanone
3-p-Methoxybenzylidene-6-hydroxy-4'-benzamidoflavanone
3-p-Methoxybenzylidene-6-hydroxy-4'-fluoroflavanone
3-p-Methoxybenzylidene-6-hydroxy-4'-chloroflavanone
3p-Methoxybenzylidene-6-hydroxy-3',4'-dichloroflavanone
3-p-Methoxybenzylidene-6-hydroxy-4'-bromoflavanone
3-p-Methoxybenzylidene-6-hydroxy-4'-iodoflavanone
3-p-Methoxybenzylidene-6-hydroxy-4'-methoxycarbonylflavanone
3-p-Methoxybenzylidene-6-hydroxy-4'-ethoxycarbonylflavanone
3-p-Methoxybenzylidene-6-hydroxy-2'-nitroflavanone
3-p-Methoxybenzylidene-6-hydroxy-3'-nitroflavanone
3-p-Methoxybenzylidene-6-hydroxy-4'-nitroflavanone
3-p-Methoxybenzylidene-6-hydroxy-3',4'-methylenedioxyflavanone.

EXAMPLE 4

A solution of 38.8 g of 3-p-methoxybenzylidene-6-hydroxy-4'-methoxyflavanone in 300 ml of pyridine is added dropwise, at 10°–15° and with stirring, to a solution of 100 ml of $POCl_3$ in 500 ml of pyridine. The mixture is stirred for a further 2 hours at 20° and is then poured into 7 l of dilute hydrochloric acid; the solution is concentrated and worked up with water and ethyl acetate, further water is added to the organic extract, the pH of the mixture is adjusted to 6 with NaOH and it is evaporated to give the disodium salt of 3-p-Methoxybenzylidene-6-hydroxy-4'-methoxyflavanone-6-phosphate.

Nuclear magnetic resonance spectrum ($DMSO+CF_3COOD$): 3.73(s), 3.81(s), 6.7(s), 6.9–7 (m) and 8.01(s) ppm (s=singlet, m=multiplet).

The following are obtained analogously:
3-Benzylidene-6-hydroxyflavanone-6-phosphate, m.p. 90°–92°
3-p-Isopropylbenzylidene-6-hydroxy-4'-isopropylflavanone-6-phosphate
3-(3,4,5-Trimethoxybenzylidene)-6-hydroxy-3',4',5'-trimethoxyflavanone-6-phosphate, m.p. 153°–155°
3-p-Acetamidobenzylidene-6-hydroxy-4'-acetamidoflavanone-6-phosphate
3-(3,4-Dichlorobenzylidene)-6-hydroxy-3',4'-dichloroflavanone-6-phosphate, m.p. 128°–130°
3-p-Methoxybenzylidene-6-hydroxy-4'-methoxyflavanone-6-phosphate
3-Benzylidene-6-hydroxy-4'-methoxyflavanone-6-phosphate and the phosphoric acid esters of the remaining 3-benzylideneflavanones mentioned in Examples 1 to 3.

EXAMPLE 5

20 ml of a solution of 14 g of phosporic acid dibenzyl ester-chloride in ether are added at −25° to a solution of 3.88 g of 3-p-methoxybenzylidene-6-hydroxy-4'-methoxyflavanone in 40 ml of pyridine, and the mixture is stirred for 1 hour at −25° and left to stand for 16 hours at −5°. The mixture is poured onto ice, acidified with hydrochloric acid to pH 4 and extracted with ether, and the extract is dried over sodium sulphate. The residue obtained from the ether solution is dissolved in 200 ml of methanol and hydrogenated over 0.3 g of 10% strength Pd/charcoal at 1 bar and 20° until absorption of hydrogen ceases. The catalyst is filtered off and the filtrate is evaporated to give 3-p-methoxybenzylidene-6-hydroxy-4'-methoxyflavanone-6-phosphate.

EXAMPLE 6

A mixture of 3.88 g of 3-p-methoxybenzylidene-6-hydroxy-4'-methoxyflavanone, 34 g of monobenzyl phosphate, 19 g of dimethylformamide chloride and 150 ml of pyridine is stirred for 2 hours at 20, allowed to stand for 16 hours at 20° and worked up analogously to Example 5. The same product is obtained.

EXAMPLE 7

A mixture of 2 ml of anhydrous phosphoric acid, 17 ml of acetonitrile and 5 ml of triethylamine is cooled to −20°, 3.6 ml of ethyl chloroformate in 4 ml of acetonitrile are added, and the mixture is stirred for 15 minutes. A solution of 3.88 g of 3-p-methoxybenzylidene-6-hydroxy-4'-methoxyflavanone in 12 ml of acetonitrile, and 4.8 ml of triethylamine are then added with stirring, the mixture is boiled for a further hour after evolution of gas has ended, and worked up analogously to Example 5 to give the same product.

EXAMPLE 8

An ethereal solution of monochlorophosphoric acid, obtained by the action of 9.4 g of $POCl_3$ on 10.2 g of 85% strength $H_3PO_4$, is added at $-10°$ to a solution of 3.88 g of 3-p-methoxybenzylidene-6-hydroxy-4'-methoxyflavanone in 20 ml of pyridine. After standing for 15 hours, the mixture is worked up analogously to Example 5. The same product is obtained.

EXAMPLE 9

A solution of 17.6 g of gentamycin sulphate in 200 ml of water is added with stirring to a solution, prepared in accordance with Example 4, of the disodium salt of 3-p-methoxybenzylidene-6-hydroxy-4'-methoxyflavanone-6-phosphate. The resulting salt of the approximate composition 1×gentamycin. 4×3-p-methoxybenzylidene-6-hydroxy-4'-methoxyflavanone-6-phosphate ("G") is filtered off and dried. IR: 1615, 1520, 1490, 1270, 1190, 1180, 1040 cm$^{-1}$.

The gentamycin salts of the remaining phosphoric acid esters mentioned in Example 4 can be obtained analogously, for example those of 3-benzylidene-6-nydroxyflavanone-6-phosphate, IR: 1670, 1620, 1490, 1070, 980, 920 cm$^{-1}$; and of 3-(3,4,5-trimethoxybenzylidene)-6-hydroxy-3',4',5'-trimethoxyflavanone-6-phosphate, IR: 1590, 1510, 1490, 1250, 1135 cm$^{-1}$.

EXAMPLE 10

The following salts of 3-p-methoxybenzylidene-6-hydroxy-4'-methoxyflavanone-6-phosphate are obtained analogously to Example 9 from the calculated amounts of the sulphates of the corresponding antibiotics and the disodium salt of this compound:
(a) with neomycin;
(b) with paromomycin;
(c) with sisomycin;
(d) with amikacin;
(e) with tobramycin;
(f) with dibekacin;
(g) with streptomycin.

The Examples below relate to pharmaceutical formulations containing compounds according to the invention:

EXAMPLE A

Tablets

A mixture of 1 kg of the mono-Na salt of 3-p-methoxybenzylidene-6-hydroxy-4'-methoxyflavanone-6-phosphate, 4 kg of lactose, 1.2 kg of potato starch, 0.2 kg of talc and 0.1 kg of magnesium stearate is compressed in the customary manner to give tablets in such a way that each tablet contains 50 mg of active compound.

EXAMPLE B

Coated tablets

Tablets are compressed analogously to Example A and are then coated in a customary manner with a coating composed of sucrose, potato starch, talc, tragacanth and a colorant.

EXAMPLE C

Capsules 10 kg of "G" are filled into hard gelatine capsules in the customary manner, so that each capsule contains active compound corresponding to 165 mg of gentamycin base.

EXAMPLE D

Ampoules 1 kg of "G" is finely micronized and suspended in 30 l of sesame oil, and the suspension is filled into ampoules, which are sealed under sterile conditions. Each ampoule contains active compound corresponding to 10 (40, 80 or 120) mg of gentamycin base.

EXAMPLE E

Implants 1.05 g of micronized "G" (corresponding to 0.2 g of gentamycin) are mixed with 8.5 g of silicone rubber monomer (medical grade Silastic 382, Dow Corning), 2 drops of polymerization catalysts are added, mixing is carried out afresh and the mixture is molded to give circular discs of diameter 20 mm and thickness 1 mm. Each disc contains 6 mg of gentamycin base.

EXAMPLE F

Fibrin-antibiotic gel

4 NIH units of thrombin (commercial preparation) are dissolved in 1 ml of aprotinin/calcium chloride solution (commercial preparation; 3,000 KIU/ml of aprotinin in 40 mmol/l of $CaCl_2$), the solution is warmed to 37°, an amount of "G" corresponding to 20 g of gentamycin base is added, and the product is mixed with the same amount of "fibrin-kleber", previously warmed to 37°, (commercial preparation; prepared by cryoprecipitation from human donor plasma; stored at $-18°$ or colder; 1 ml of the solution contains on average 90 mg of thrombin-precipitatable protein, total albumin content of the solution about 10% by weight; thawed about 20–30 minutes before the intended use). The mixture is allowed to solidify in stainless steel cylinders (internal diameter 6 mm, height 10 mm) (1 ml for 3 cylinders). The cylinders of gel formed are then ejected from the molds.

EXAMPLE G

Inhalation capsules 5 kg of the mono-Na salt of 3-p-methoxybenzylidene-6-hydroxy-4'-methoxyflavanone-6-phosphate and 5 kg of lactose are mixed, and the mixture is filled into capsules in the customary manner so that each capsule contains 50 mg of active compound. The capsules can be applied by means of an inhaler.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. A flavanone of the formula

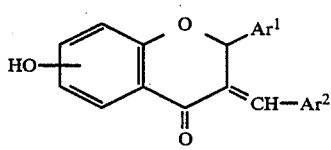

wherein
each of $Ar^1$ and $Ar^2$ independently is phenyl, or phenyl (a) monosubstituted to trisubstituted by OH, alkyl, alkoxy, alkanoylamino, halogen, COOalkyl, $NO_2$ or a combination thereof; (b) substituted by methylenedioxy; or (c) substituted as in (a) and (b);
each alkyl, alkoxy and alkanoyl group is 1-7 C atoms, with the proviso that the HO group on the benzofused ring is in the 6-position, only when at least one of $Ar^1$ and $Ar^2$ is substituted phenyl, or a phosphoric acid ester thereof or a pharmaceutically acceptable salt of the flavanone or phosphoric ester.

2. A flavanone of claim 1 wherein $Ar^1$ and $Ar^2$ are the same.

3. A flavanone of claim 1 wherein the 6-position is occupied by OH.

4. A flavanone of claim 1 wherein either $Ar^1$ or $Ar^2$ is phenyl or phenyl which is mono-substituted by OH, alkyl, alkoxy or alkanoylamino each of 1-4 C atoms, F, Cl, Br, I, COOalkyl wherein alkyl is of 1-4 C atoms, $NO_2$ or methylenedioxy, or disubstituted by alkoxy of 1-4 C atoms or by Cl, or trisubstituted by alkoxy of 1-4 C atoms.

5. A flavanone of claim 1 wherein either $Ar^1$ or $Ar^2$ is phenyl, isopropylphenyl, methoxyphenyl, acetamidophenyl, chlorophenyl, dichlorophenyl or trimethoxyphenyl;

6. A flavanone of claim 1 wherein either $Ar^1$ or $Ar^2$ is phenyl or methoxyphenyl.

7. A flavanone of claim 1 wherein either $Ar^1$ or $Ar^2$ is p-methoxyphenyl.

8. A flavanone of claim 1 wherein $Ar^1$ and $Ar^2$ are each phenyl or phenyl which is monosubstituted by OH, alkyl, alkoxy or alkanoylamino each of 1-4 C atoms, F, Cl, Br, I COOalkyl wherein alkyl is of 1-4 C atoms, $NO_2$ or methylenedioxy, or disubstituted by alkoxy of 1-4 C atoms or Cl, or trisubstituted by alkoxy of 1-4 C atoms.

9. A flavanone of claim 1 wherein $Ar^1$ and $Ar^2$ are each phenyl, isopropylphenyl, methoxyphenyl, acetamidophenyl, chlorophenyl, dichlorophenyl or trimethoxyphenyl.

10. A flavanone of claim 1 wherein $Ar^1$ and $Ar^2$ are each phenyl or methoxypheyl.

11. A flavanone of claim 1 wherein $Ar^1$ and $Ar^2$ are each p-methoxyphenyl.

12. A compound of claim 1 which is a phosphate.

13. A compound of claim 1 which is a pharmaceutically acceptable salt.

14. A compound of claim 12 which is a pharmaceutically acceptable salt.

15. The gentamycin salt of 3-p-methoxybenzylidene-6-hydroxy-4'-methoxyflavanone-6-phosphoric acid ester, a compound of claim 1.

16. A salt of claim 13 with an aminoglycoside antibiotic.

17. A salt of claim 14 with an aminoglycoside antiobiotic.

18. A pharmaceutical composition comprising an anti-allergically effective amount of a compound of claim 1 and a pharmaceutically acceptable carrier.

19. A composition of claim 18 wherein the amount of flavanone is 5-1000 mg.

20. A method of achieving an antiallergic effect comprising administering a compound of claim 1.

21. A method of achieving an antibiotic effect comprising administering a compound of claim 13 which is a salt of an aminoglycoside antibiotic.

22. A method of achieving an antibiotic and an antiallergic effect comprising administering a compound of claim 13 which is a salt of an aminoglycoside antibiotic.

23. A pharmaceutical composition comprising an antibiotically effective amount of a compound of claim 1 and a pharmaceutically acceptable carrier.

24. A composition of claim 23 wherein the amount of flavanone is 5-1000 mg.

* * * * *